United States Patent [19]

Holst et al.

[11] 4,068,067
[45] Jan. 10, 1978

[54] PROCESS FOR THE PRODUCTION OF WATER-ADSORBING CELLULOSE ETHERS

[75] Inventors: Arno Holst; Helmut Lask; Michael Kostrzewa, all of Wiesbaden, Germany

[73] Assignee: Hoechst Aktiengesellschaft, Germany

[21] Appl. No.: 683,968

[22] Filed: May 6, 1976

[30] Foreign Application Priority Data

May 7, 1975   Germany .............................. 2520336

[51] Int. Cl.$^2$ ...................... C08B 11/00; C08B 11/20; C08B 11/193; C08B 15/10
[52] U.S. Cl. ...................................... 536/87; 128/296; 260/17 A; 536/84; 536/88
[58] Field of Search .................. 260/17 A; 536/84, 87, 536/88

[56] References Cited

U.S. PATENT DOCUMENTS

| | | | |
|---|---|---|---|
| 1,884,629 | 10/1932 | Dreyfus | 536/98 |
| 2,517,577 | 8/1950 | Klug et al. | 536/98 |
| 2,667,480 | 1/1954 | Branon et al. | 536/98 |
| 3,069,409 | 12/1962 | Henry et al. | 536/98 |
| 3,085,087 | 4/1963 | Henry et al. | 536/98 |
| 3,589,364 | 6/1971 | Dean et al. | 128/284 |
| 3,936,441 | 2/1976 | Holst et al. | 536/98 |
| 3,965,091 | 6/1976 | Holst et al. | 536/98 |

OTHER PUBLICATIONS

"The New Cellulose Solvent: Dimethyl Sulfoxide—Paraformaldehyde," Johnson et al., 39th Executive Conference, the Institute of Paper Chemistry, Appleton, Wisconsin, May 8, 1975, pp. 78-80, 82 and 83.

Primary Examiner—Ronald W. Griffin
Attorney, Agent, or Firm—James E. Bryan

[57] ABSTRACT

This invention relates to an improvement in the process for the production of water-adsorbing, but at least partially water-insoluble cellulose ethers in which cellulose is alkalized in a liquid reaction medium and etherified in a manner such that by etherification only an at least largely water-soluble carboxymethyl cellulose, carboxymethyl hydroxyethyl cellulose, hydroxyethyl cellulose or methyl hydroxyethyl cellulose is produced, and in which the cellulose is reacted in an alkaline reaction medium before, during, or after the etherification with a modification agent reactive with the still free hydroxyl groups of the cellulose anhydro glucose groups, said modification agent having one of the formulae

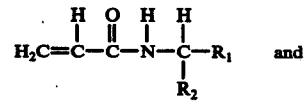

and

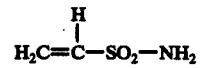

in which $R_1$ is hydroxyl, an acylamino or esterified carbamino group, and $R_2$ is hydrogen or a carboxyl group, the improvement comprising effecting alkalization, etherification, and modification in a liquid reaction medium other than isopropyl alcohol.

3 Claims, No Drawings

PROCESS FOR THE PRODUCTION OF WATER-ADSORBING CELLULOSE ETHERS

The present invention relates to a process for the production of water-adsorbing, but at least partially water-insoluble, cellulose ethers.

It is known, for example from U.S. Pat. No. 3,589,364, to cross-link water-soluble carboxymethyl cellulose, which can be produced by etherification of cellulose with monochloroacetic acid, in order to obtain a cellulose ether which is, at least in part, water-insoluble, but which has the capacity of adsorbing relatively large quantities of water, and of simultaneously swelling. The cross-linking may take place before, after or simultaneously with, the etherification. Reaction agents which are polyfunctional towards cellulose are used as cross-linking agents, for example epoxy compounds, polychlorinated higher alcohols, or divinyl sulfone. Epichlorohydrin is preferably used, because it achieves simultaneous cross-linking and etherification. Cross-linking takes place in the presence of a relatively small quantity of water, either in a semi-dry environment, or in the presence of relatively large quantities of an inert organic diluent, for example isopropanol present in a quantity 40 times that of the cellulose. At standard temperature, cross-linking requires many hours, e.g. 18 hours; at a higher temperature the reaction is more rapid, but even at temperatures over 70° C several hours are required, e.g. 3.5 hours.

In U.S. application Ser. No. 524,822, filed Nov. 18, 1974, now U.S. Pat. No. 3,965,091, issued June 22, 1976, having the title "Process for the Production of Water-Adsorbing but Water-Insoluble Cellulose Ethers", a process is disclosed by means of which modified cellulose ethers may be obtained in a relatively short reaction time. According to this process water-adsorbing, but largely water-insoluble, i.e., more than 50 percent by weight insoluble, cellulose ethers are produced by alkalizing cellulose in the presence of alkali and isopropanol as a reaction medium, in which process the cellulose reacts with an etherification agent in a manner such that by means of etherification only a water-soluble carboxymethyl cellulose, carboxymethyl hydroxyethyl cellulose, hydroxyethyl cellulose or methyl hydroxyethyl cellulose would be produced and in which a modification takes place before, simultaneously with or after, the etherification with a compound reactive with the still free hydroxyl groups of the cellulose anhydro glucose groups in an alkaline medium, the modification agent being a compound having one of the formulae

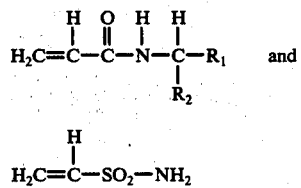

and $$H_2C=C-SO_2-NH_2 \quad \text{II}$$
$$\phantom{H_2C=C}|$$
$$\phantom{H_2C=C}H$$

in which

R₁ is a hydroxyl group, an acylamino group or an esterified carbamino group, and R₂ is a hydrogen or a carboxyl group.

It now has been found that the aforementioned cellulose ethers also are obtained within a relatively short modification time, if alkalization, etherification and modification are carried out in a liquid reaction medium other than isopropyl alcohol.

In the process according to the invention, the known etherification process is used in which alkali cellulose is etherified in a manner such that a cellulose ether is produced which is at least largely water-soluble. For practical reasons, alkali cellulose produced from an aqueous NaOH solution is almost exclusively used, but the etherification also may be carried out with alkali cellulose produced from an aqueous KOH solution or LiOH solution. Preferred etherification agents for the production of water-soluble cellulose ethers are sodium monochloroacetate, monochloroacetic acid, methyl chloride, ethylene oxide and propylene oxide, either singly or in admixture, and ethyl chloride, especially when mixed with ethylene oxide or propylene oxide.

The process according to the invention includes an etherification reaction as well as a modification reaction. The modification reaction is carried out in a manner such that at least 20 percent by weight of the cellulose ether is no longer water-soluble, but the product is swellable with water. Such an additional modification reaction is known as well. In the process according to the invention the modification agents of the aforementioned application are used, for example N-methylol acrylamide,
N-(acrylamido methylene)-acetamide,
N-(acrylamido methylene)-formamide,
N-(acrylamido methylene)-amylurethane,
N-(acrylamido methylene)-methylurethane,
N-(acrylamido carboxy methylene)-ethylurethane,
N-(acrylamido methylene)-methoxyethylurethane, and
vinyl sulfonamide.

Of these agents, up to 100 parts by weight, preferably however, less than 25 parts by weight, are used per 100 parts by weight of cellulose.

If a modified cellulose ether having a high water retention value (WRV) is to be obtained, an organic solvent is advantageously used as a liquid reaction medium, for example dioxane, methyl ethyl ketone, ethanol, acetone or tertiary butyl alcohol, which solvent moreover does not significantly react with the reaction partners or reacts not at all.

Cellulose ethers produced and modified in a purely aqueous reaction medium can adsorb water very rapidly. For their production, a dry alkali cellulose is preferred, i.e. an alkali cellulose that is produced by uniformly mixing pulverized cellulose with the necessary amount of alkali by spraying with a concentrated, i.e. at least 20 percent aqueous alkali hydroxide solution, the alkali cellulose obtained being an almost dry powder. However, dip alkali cellulose also may be used, i.e. alkali cellulose produced by dipping cellulose plates or cellulose webs in an aqueous alkali hydroxide solution and then squeezing and shredding them. Such an alkali cellulose is composed of a granular, non-agglomerating mixture. If a purely aqueous reaction medium is employed, the modification preferably is not deferred until after the etherification, but is carried out simultaneously with the etherification process. In a purely aqueous reaction medium, alkylene oxides, especially ethylene oxide, react very rapidly. Thus, accumulation of heat may lead to discolored products, but for some practical applications this is not a disadvantage. Local overheating may be prevented by providing a uniform heat exchange. In mixed etherification processes, it is possible for the other etherification agent to assume the role of a heat distributor.

Similar to the hitherto known processes, the process of the invention leads to modified products which contain a certain water-soluble portion. For many purposes this is immaterial, so that it is usually unnecessary to remove the water-soluble portion. In the examples below, the quantity of the portion of the modified cellulose is given that is soluble in pure water at 20° C.

The modified cellulose ethers produced by the process of the invention may be used for various technical purposes, for example they may serve as adsorbing materials in surgical and hygienic bandages, or as dehydrating agents, for example in aqueous emulsions.

In the process according to the invention, sufficiently modified products are obtained within a very short time, i.e. in about one hour, at moderate temperatures, preferably up to about 80° C. Products with varying water retention values are obtained, depending upon the etherification and modification conditions. Therefore, different requirements can be met. The quantity of water retained may be extremely high and may amount, for example, to 60 times the weight of the modified cellulose ether. The water adsorbed is so firmly attached to the modified product that it cannot be removed therefrom, even if a centrifugal force is applied which corresponds to 2000 times the acceleration due to gravity.

As a further advantage of the process according to the invention products are obtained which have a high water retention value relative to the quantity of modification agent used.

In the examples below all percentages are by weight. Alkalization, etherification and modification are carried out at the temperatures given and while the reactants are thoroughly mixed. The abbreviation "WRV" means water retention value or capacity. It is given in percent by weight, based upon the dry weight of the water-insoluble portion.

EXAMPLE 1

In a paddle mixer 1000 g of cellulose are alkalized with 1830 g of an aqueous NaOH solution (28 percent) for 45 minutes at 20° C. Then, 1368 g of sodium monochloroacetate are added to the alkali cellulose and both are mixed for 5 minutes. Then, 200 g of a 60 percent aqueous solution of N-methylol acrylamide (0.2 mole/mole of cellulose) are added and etherification and modification are carried out while the material is constantly mixed for one hour at 70° C. After cooling, the reaction product is neutralized towards phenolphthalein by means of acetic acid and is filtered. The solid product is washed salt-free by means of aqueous methanol (80 percent) and dried at 60° C. The modified carboxymethyl cellulose has a WRV of 10,800 and a soluble protion of 25.9%.

EXAMPLE 2

In a paddle mixer 500 g of cellulose are alkalized with 416 g of an aqueous NaOH solution (28 percent) for 45 minutes at 20° C. A mixture of 100 g of vinyl sulfonamide (0.32 mole/mole of cellulose) and 271 g of monochloroacetate is added to the alkali cellulose and etherification and modification are carried out while the material is constantly mixed for one hour at 70° C. The reaction product is treated as described in Example 1. The modified carboxymethyl cellulose has a WRV of 17,040 and a soluble portion of 47.6%.

EXAMPLE 3

The procedure of Example 2 is followed, except that the modification is carried out with 125 g of a 50 percent aqueous solution of acrylamido methylene formamide (0.165 mole/mole of cellulose). The modified carboxymethyl cellulose has a WRV of 2,705 and a soluble portion of 26.8%.

EXAMPLE 4

The procedure of Example 1 is repeated, however, using 50 g of a 60 percent aqueous solution of N-methylol acrylamide. The modified carboxymethyl cellulose has a WRV of 18,400 and a soluble portion of 63.2%.

It will be obvious to those skilled in the art that many modifications may be made within the scope of the present invention without departing from the spirit thereof, and the invention includes all such modifications.

What is claimed is:

1. In the process for the production of water-adsorbing, but at least partially water-insoluble cellulose ethers in which cellulose is alkalized in a liquid reaction medium and etherified in a manner such that by etherification only an at least largely water-soluble carboxymethyl cellulose, carboxymethyl hydroxyethyl cellulose, hydroxyethyl cellulose or methyl hydroxyethyl cellulose is produced, and in which the cellulose is reacted in an alkaline reaction medium before, during, or after the etherification with a modification agent reactive with the still free hydroxyl groups of the cellulose anhydro glucose groups, said modification agent having one of the formulae

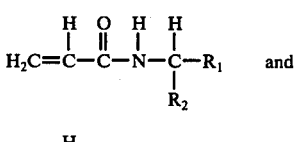

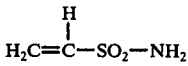

in which $R_1$ is hydroxyl, an acylamino or esterified carbamino group, and $R_2$ is hydrogen, or a carboxyl group, the improvement comprising effecting alkalization, etherification, and modification in a liquid reaction medium selected from the group consisting of the organic solvents dioxane, methyl ethyl ketone, ethanol, acetone and tertiary butyl alcohol, and the solvent water.

2. A process according to claim 1 including effecting alkalization, etherification, and modification in a substantially pure aqueous reaction medium.

3. A process according to claim 1 including modifying the cellulose ether to form a cellulose ether which is more than 50 percent by weight insoluble.

* * * * *